United States Patent
Nayeri

(10) Patent No.: US 9,157,920 B2
(45) Date of Patent: Oct. 13, 2015

(54) METHOD FOR DETERMINING BIOLOGICALLY ACTIVE HGF

(75) Inventor: Fariba Nayeri, Linkoping (SE)

(73) Assignee: PEAS Institut AB, Linkoping (SE)

( * ) Notice: Subject to any disclaimer, the term of this patent is extended or adjusted under 35 U.S.C. 154(b) by 959 days.

(21) Appl. No.: 13/380,583

(22) PCT Filed: Jun. 28, 2010

(86) PCT No.: PCT/SE2010/050734
§ 371 (c)(1),
(2), (4) Date: Dec. 23, 2011

(87) PCT Pub. No.: WO2010/151222
PCT Pub. Date: Dec. 29, 2010

(65) Prior Publication Data
US 2012/0094310 A1  Apr. 19, 2012

(30) Foreign Application Priority Data
Jun. 26, 2009  (SE) ...................................... 0950499

(51) Int. Cl.
G01N 33/74 (2006.01)
C08L 5/02 (2006.01)
C08L 5/08 (2006.01)
C08L 5/10 (2006.01)
C08L 5/12 (2006.01)

(52) U.S. Cl.
CPC . *G01N 33/74* (2013.01); *C08L 5/02* (2013.01); *C08L 5/08* (2013.01); *C08L 5/10* (2013.01); *C08L 5/12* (2013.01); *G01N 2333/4753* (2013.01); *G01N 2400/40* (2013.01)

(58) Field of Classification Search
None
See application file for complete search history.

(56) References Cited

U.S. PATENT DOCUMENTS

2003/0036103 A1* 2/2003 Pillarisetti et al. ............ 435/7.23
2005/0037431 A1* 2/2005 Kirchhofer et al. ............ 435/7.1

FOREIGN PATENT DOCUMENTS

| WO | 0040747 A1 | 7/2000 |
| WO | 2005031365 A2 | 4/2005 |
| WO | 2006043892 A1 | 4/2006 |
| WO | 2007091159 A2 | 8/2007 |

OTHER PUBLICATIONS

Craven (2002) Am J Path 160:815-822.*
Volpi, et al., "Detection of submicrogram quantities of glycosaminoglycans on agarose gels by sequential staining with toluidine blue and Stains-All", Electrophoresis, Dec. 2002, vol. 23, No. 24, pp. 4060-4066.
Kato, et al., "Hepatocyte growth factor immobilized onto culture substrates through heparin and matrigel enhances DNA synthesis in primary rat hepatocytes", Experimental Cell Research, 1994, vol. 211, No. 1, pp. 53-58.
Chupa, et al., "Vascular cell responses to polysaccharide materials: in vitro and in vivo evaluations", Biomaterials, Elsevier Science Publishers BV, Nov. 15, 2000, vol. 21, No. 22, pp. 2315-2322.
Horie, et al., "Biological role of HGF/MET pathway in renal cell carcinoma", Journal of Urology, Mar. 1, 1999, vol. 161, No. 3, pp. 990-997.
Kitajima, et al., "A fusion protein of hepatocyte growth factor for immobilization to collagen", Biomaterials, Apr. 2007, vol. 28, No. 11, pp. 1989-1997.
Ijima, et al., "Primary rat hepatocytes form spheroids on hepatocyte growth factor/heparin-immobilized collagen film and maintain high albumin production", Biochemical Engineering Journal, Oct. 1, 2009, vol. 46, No. 2, pp. 227-233.
Ashikari, et al., Characterization of Heparan Sulfate Oligosaccharides that Bind to Hepatocyte Growth Factor, The Journal of Biological Chemistry, 1995, vol. 270, No. 49. pp. 29586-29593.
Santos, et al., The renal clearance of dextran sulfate decreases in puromycin aminonucleoside-induced glomerulosis: a puzzle observation, Clinica Chimica Acta, 2007, vol. 383, pp. 116-125; paragraph 2.4.

* cited by examiner

*Primary Examiner* — Chris L Chin
*Assistant Examiner* — Richard Moerschell
(74) *Attorney, Agent, or Firm* — Pierce Atwood LLP; Kevin M. Farrell

(57) ABSTRACT

The present invention relates to a for determining the presence, absence or amount of biologically active or inactive HGF in a sample, comprising the steps: bringing the sample in contact with a gel comprising a HGF binding component of the extracellular matrix or cell membrane, adding toluidine blue to the gel, correlating the color of the gel and/or a liquid in contact with the gel with the presence, absence or amount of biologically active HGF in the sample. It also relates to a kit of parts comprising toluidine blue and a gel comprising at least one HGF-binding component of the extracellular matrix or cell membrane, such as a proteoaminoglycan or a glucosaminoglycan, and optionally buffers, vials and sampling instruments and to a gel comprising at least one HGF-binding component of the extracellular matrix or cell membrane, such as a proteoaminoglycan or a glucosaminoglycan, toluidine blue and HGF.

7 Claims, 2 Drawing Sheets

METHOD FOR DETERMINING BIOLOGICALLY ACTIVE HGF

FIELD OF THE INVENTION

The present invention is in the technical field of methods for detecting presence of growth factors such as hepatocyte growth factor (HGF) in biological samples. It also relates to products for performing such methods.

BACKGROUND OF THE INVENTION

Hepatocyte growth factor (HGF) is a unique growth factor, which is unrelated to other well-known polypeptide mitogens. It is a protein expressed in the mesenchymal cells such as lung macrophages and fibroblasts, Kupffer cells in the liver and leukocytes. HGF is secreted in response to cell damage and appears to be important for the regeneration of certain organs and healing of wounds. It is a heterodimer, having disulphide bonded heavy and light chains of approximately 60 and 30 kDa respectively, first synthesized as an inactive precursor. The precursor is cleaved to an active protein in the damaged organ by a specific activator. HGF acts paracrinally, i.e. it affects adjacent cells, as well as endocrinally, i.e. it has a long-distance. The target cells of HGF are fully developed epithelial cells. HGF is produced and is present in high concentrations at sites of organ damage.

The systemic and local production of HGF in various infectious diseases has been studied and high serum HGF concentrations have been observed during acute infectious diseases such as gastroenteritis, sepsis, pneumonia, skin and soft tissue infections and pyelonephritis. Simultaneous with enhanced systemic production of HGF, high HGF concentrations have been found in cerebrospinal fluid during meningitis. Raised HGF concentrations in exhaled breath condensate in patients with pneumonia, which had no correlation to serum levels of HGF, indicated a local production of HGF during pneumonia. Furthermore the stability of HGF in serum has been studied and HGF was found to be very stable in diluted feces samples and several freeze-thaw cycles, different buffers or several years of storage at −20° C. did not affect feces HGF concentrations significantly. High amounts of HGF in feces during diarrhea have been shown to possibly indicate that patient suffers from a transmittable gastroenteritis. Further, monitoring of HGF levels before and after treatment during infectious diseases has been shown to possibly reveal therapeutic failure at an early stage.

Recognizing the clinical importance and differences between recommended therapies, differential diagnosis between inflammatory disorders in the body has been the subject of several investigations. One major clinical problem is determining whether infection or other inflammatory disorders cause the disease. There are several markers that typically are used by physician to establish the right diagnosis such as microscopic analysis and culture of body fluids, white blood cell count, C-reactive protein, plasma procalcitonin and lactate. However, there are still no golden standards to be used. Problems in establishing correct diagnosis occurs daily while treating inflammatory disorders in bowel, ulcers, joint diseases, CNS disorders, peritoneal, pleural and pericardial effusions, among others. The amounts of routine markers such as CRP and WBC might be high in several disorders and cultures are not always positive in spite of an infection. High amounts of HGF and its application in diagnosis and prognosis of infectious diseases are discussed in PCT application PCT/SE2001/001831. Yet in these studies, the whole amount of HGF in the body fluids was determined by ELISA method.

Various studies about HGF have been reported. Some studies have used determination of HGF in plasma/serum and urine for diagnosis and screening of diseases such as acute renal deficiency, myocardial infarction, carcinoma of bladder, acute pancreatitis and acute and chronic lung diseases. For this reason, previously described methods such as ELISA and Western blotting have been used. Detection of high amounts of cytokines during inflammatory diseases is not a unique finding. However, in some cases, determination of HGF has been found to be a sensitive method that could detect specific clinical problems much easier than the routine methods (PCT application PCT/SE2001/001831).

The previous described methods such as ELISA and Western blotting are based on an interaction between HGF in the samples and an antibody that binds specifically to HGF. In ELISA, the amount of HGF single-chain and double-chain is determined. By Western-blotting the quality of HGF in the body fluid is determined by detection of apparent molecular masses present in the sample. However the methods are cumbersome and laborious.

The innovative use of biosensors is useful, inexpensive and rapid in this area of analysis. Surface plasmon resonance (BIACORE®) method can be used for the detection of HGF in feces (WO2005/031365). The technique is able to detect HGF levels and quality in a single run.

In the case of infection: In different organs, the levels of HGF are increased locally at the site of infection. The whole amount of protein might be detected by ELISA. Using Biacore® technology, detection of the level of interaction (signals) to monoclonal, polyclonal antibodies to HGF as well as heparan sulphate proteoglycan (HSPG) immobilized to the chip, is high and it correlates positively to the results obtained by ELISA.

In the case of chronic inflammation: In spite of high amounts of HGF in samples that might be found by ELISA, non-significant correlation between ELISA and the results obtained by Biacore® is observed. It might be no or very low signals detected by Biacore® that shows a weak interaction to the ligands. The interaction to c-met protooncogene receptor might be high and the signals correlate positively to the level of immobilization. There is low signal rate at the HSPG channel. Adding HSPG or dextran sulphate to the samples at least 10 minutes prior to analysis might not diminish the signal at the HSPG channel. The protein might be biologically inactive.

The growth factors and cytokines such as Hepatocyte growth factor produced during injuries are released endocrinally and produced locally by the neighbor mesenchymal cells. The protein interacts with the high affinity cell binding specific receptor and sends signal into the cell resulting in regeneration of injured organ. In the case of HGF a non-specific receptor on the cell membrane and extracellular matrix (ECM) is needed to capture the cytokine and make it available to the specific receptor (c-Met receptor). Therefore the variants of HGF which show no affinity to HSPG or other proteoaminoglycans are not captured by ECM after release and might not interact with the specific receptor. Thus the protein might act as inactive in spite of high affinity to c-Met receptor.

In our previous works we have studied HGF by SDS-page, Western blot, ELISA and SPR and shown that the HGF protein (endogenous or recombinant) which did not bind to proteoaminoglycan (HSPG, heparan sulphate) or dextran sulphate, had no biological effect in the in-vivo (hair growth mice) or in-vitro biological activity methods (CCL-53.1 cells) used in our group. We have seen differences in patients with acute infection compared to chronic inflammation in binding affinity to HSPG in SPR method. Our primary conclusion is that in patients with chronic inflammation the high hierarchy cytokines such as HGF are inactivated and therefore they might need exogenous biologically active HGF to stimulate regeneration. As an example treatment with exogenic HGF has been shown to be beneficial in treatment of some cases of chronic leg ulcers (PCT application PCT/SE2001/001831). HGF has been found to enhance migration of healthy neighbor skin epithelial cells towards the damaged area by changing the cytoskletal structure of cells in vitro. An enhanced expression of met proto-oncogene receptor (c-met) in the ulcer area of patients with chronic ulcers is seen. Treatment with exogenous HGF decreased c-met expression significantly. There was a negative correlation between biologically active endogenous HGF concentration in the ulcer secrete and met proto-oncogene receptor (c-met) expression. Treatments with exogenous HGF in the patients with a low amount of endogenous HGF and high met proto-oncogene receptor (c-met) expression caused vascular proliferation and ulcer area reduction. This model of organ injury in the skin and the related events might be true in other organ tissues as well.

SUMMARY OF THE INVENTION

In a first aspect the present invention relates to a method for determining the presence, absence or amount of biologically active HGF in a sample, comprising bringing a HGF containing sample in contact with a gel comprising at least one HGF-binding component of the extracellular matrix (ECM) or cell membrane, such as a proteoaminoglycan or a glucosaminoglycan.

In a second aspect, the present invention relates to a kit of parts comprising toluidine blue and a gel comprising at least one HGF-binding component of the extracellular matrix (ECM) or cell membrane, such as a proteoaminoglycan or a glucosaminoglycan, and optionally buffers, vials and sampling instruments for performing the method according to the first aspect.

In a third aspect, the invention relates to a gel comprising at least one HGF-binding component of the extracellular matrix (ECM) or cell membrane, such as a proteoaminoglycan or a glucosaminoglycan, toluidine blue and HGF.

DEFINITIONS AND ABBREVIATIONS

Figure 1:
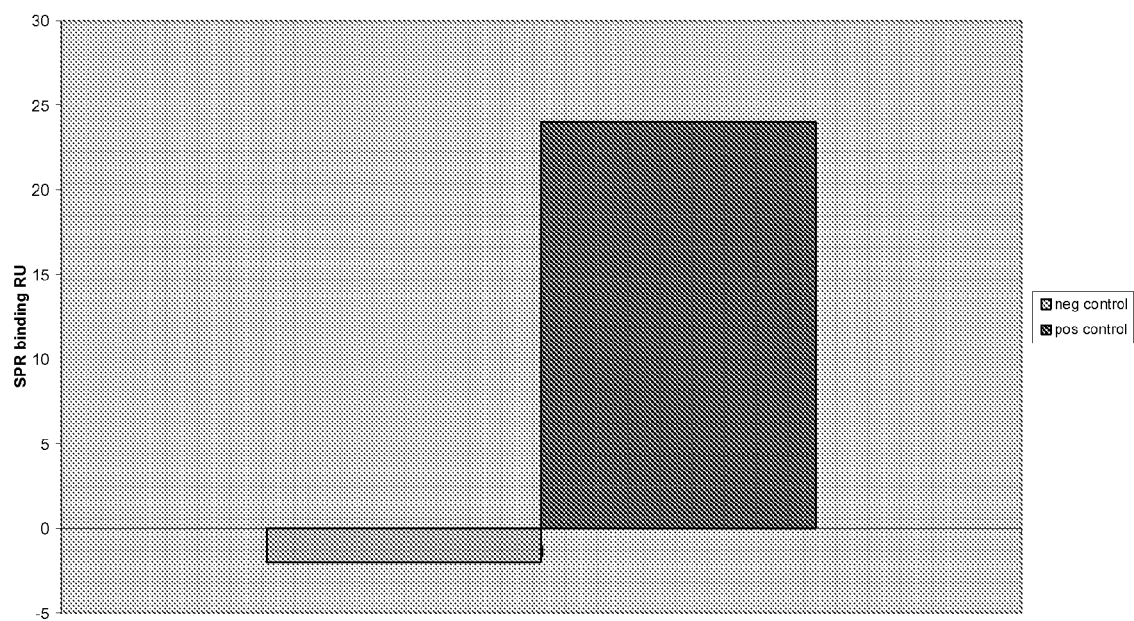
FIG. 1: Comparison between patients with normal Cerebrospinal fluid (CSF)(neg control) and patients with meningitis (pos control) in binding affinity of CSF-HGF to HSPG in Biacore® system.

The quality of HGF indicates the ability of HGF to bind to the extracellullar matrix and exert its biological effects in vivo.
HGF means Hepatocyte Growth factor, also called Scatter Factor.
ECM means extracellular matrix.
HSPG means heparan sulphate proteoglycan.

A HGF binding component of the extracellular matrix or cell membrane, or ECMCM component for short, means a component of the extracellular matrix or cell membrane that shows affinity for HGF in vivo and thus facilitates the biological activity of HGF, and analogues of such components showing equivalent affinity characteristics towards HGF. Examples of such components are glucosaminoglycans, proteoaminoglycans, HSPG and dextran sulphate.

MQ, or Milli-Q, refers to water that has been purified and deionized to a high degree.

The "absence" of biologically active HGF from a sample shall not be construed as an absolute non-presence of biologically active HGF, but rather as such a low level that there is essentially no biological effect of said HGF.

"Dexakt" refers to the invention

DETAILED DESCRIPTION OF THE INVENTION

Hepatocyte Growth Factor in its biologically active form has high affinity to proteoaminoglycans such as heparan sulphate proteoglycan (HSPG) and dextran sulphate. This affinity resembles the binding of growth factor to the cell membrane prior to interaction to its membrane-binding receptor.

This affinity is utilized in the following aspects and embodiments of the present invention.

Based on the previous results using the observations from SPR method that showed that cytokines with high affinity to ECM components were released during acute infection, the present inventors have invented a platform by addition of amounts of proteoaminoglycan in a base gel. The affinity of protein to proteoaminoglycan is then visualized by colour changes on addition of an indicator solution containing toluidine blue.

The invention uses a gel containing a gelling agent and a HGF binding component of the extracellular matrix or cell membrane, preferably dextran sulphate or HSPG.

The following recipe is presently preferred:
100 mg agaros gel is solved in 9 ml deionized sterile water+1 ml PBS
1 ml of proteoaminoglycan (preferably dextran sulphate or heparan sulphate proteoglycan) solution containing 10 mg/ml dextran sulphate
Or:
1—100 mg gelatin powder is solved in 9 ml deionized sterile water+1 ml PBS
2—10 mg dextran sulphate
Add all and boil in microwave The gel might be easily divided in small polypropiolen eppendorf tubes 12 ul in each tube when still warm and then put in the refrigerator in 10 minutes. It is ready to use. It is possible to use empty ELISA plates with 12 ul gel in each well in order to make a plate to test 100 samples. Preferably, at least 50 ul sample is added to each tube/well.

Further embodiments of the gel used in the invention are given in the Examples.

As substrate toluidine blue 100 mg powder is solved in 15 ml deionized sterile water. Add 20 µl of this solution in 30 ml deionized sterile water. After 5 minutes 200 ul toluidine blue solution is added and the results are available after 2 minutes. ELISA reader spectrophotometer might be used to document the results.

Other components of extracellular matrix (e.g. glucosaminoglycans) might be used as well but Dextran sulphate is less costly and shows similar results. Sterile preparation of gel increases the stability and is thus preferred. The stability is at least one month after preparation when stored in 4-8° C. or −20° C.

The inventive method comprises addition of a test sample to the gel, whereby biologically active HGF attaches to dextran sulphate. The remaining sample is removed, e.g. by cotton tips or washing.

A substrate such as toluidine blue is then added to the washed gel. During interaction between ECMCM component and toluidine blue the colour of toluidine blue changes to purple red. There is a competition between biologically active HGF and toluidine blue in interaction with ECM component. If the sample contains biologically active HGF that binds to ECMCM component toluidine blue is inhibited to interact with the ECMCM component and the colour of the solution remains blue. The range of blue colour depends on the affinity of HGF to the ECM component. In the control wells with no HGF or biologically inactive HGF, the ECMCM component is still able to interact with toluidine blue and the colour turns purple red. By this method presence of HGF in a sample is detected within 5-10 minutes.

The amount of HGF can be determined by the difference in bluish colour using an Elisa photospectrometer or similar instrument. Optionally, one or more reference solutions of known HGF content is used to evaluate the result. A negative reference may be e.g. water or PBS. A positive reference may be a healthy body fluid sample or a HGF containing product, with known content and activity of HGF.

The invention also relates to a kit of parts comprising a gel comprising an ECMCM component and an indicator solution comprising toluidine blue. Such a kit may further include other components useful for performing the inventive method, such as buffers, vials, sampling instruments for taking samples such as tissue biopsies, blood samples, urine samples, faeces samples or any other sample that may be used in the inventive method. The kit may further include instructions for performing the method according to the invention.

The invention also relates to a gel that is being used or has been used in the method according to the invention and thereby indicates the presence, absence or amount of biologically active HGF in a sample. Such a gel comprises an ECMCM component, toluidine blue and HGF.

By the method of the invention it is possible to rapidly distinguish an acute inflammation such as bacterial infection in organ from a chronic inflammation.

The methods and products according to the invention may be used to analyse the following:

- Differences between septic arthritis and non-septic or reactive arthritis in joints
- Differences between acute transmittable gastroenteritis and chronic inflammatory bowel diseases or other causes of diarrhea
- Differences between acute septic meningitis and non-specific pleocytosis in cerebrospinal fluid
- Differences between acute renal insufficiency as well as pyelonephritis and distal urinary tract infection as well as chronic renal injury
- Differences between pneumonia and chronic obstructive lung disease in exhaled breath condensate
- Differences between septic inflammation in pleural effusion and ascites and non-septic inflammation
- Presence of HGF in serum and plasma
- Standard evaluation of biologically active HGF in medications and blood products.
- Monitoring of antibiotic treatment.
- Locate the infectious focus during disease The invention is further described by the following examples. The examples are illustrative and should not be construed as limiting the scope of the invention, which is that defined by the appended claims.

EXAMPLE 1

Production of Gels Comprising HGF Binding Components

Recipe 1, Dextran Sulphate Gel
Remark: Sterile process
5 mg Dextran sulphate sodium salt (Sigma Aldrich)
50 mg Agarose powder (Sigma aldrich)
5 ml (270 ml MQ+30 ml PBS pH 7.4)
Heat in microwave oven
Divide 12-15 µl in 1-2 ml tubes (eppendorf)
Keep in 4-8° C. until usage
Recipe 2, Dextran Sulphate Gel with Chitosan
    1—100 mg agarose gel is solved in 9 ml deionized sterile water+1 ml PBS
    2—100 mg chitosan is solved in 4 ml glycin 2.0
    3—1 ml of proteoaminoglycan (preferably dextran sulphate or heparan sulphate proteoglycan) solution containing 10 mg/ml dextran sulphate
    4—Add all and boil in microwave
    5—Separate the clump
    6—Divide the clear liquid in wells 25-100 µl and let it solidify during several minutes
    The dextran sulphate gel is ready to use.
Recipe 3, HSPG Gel
100 µl heparan sulfat proteoglycan (HSPG) a: 400 µl(ml) Sigma Aldrich (H7640)
50 mg agarose powder Sigma Aldrich
5 ml (270 ml MQ+30 ml PBS pH 7.4)
Heat in microwave.
Divide 15 µl in wells
Indicator Solution As substrate toluidine blue powder (Sigma Aldrich) 100 mg is solved in 15 ml deionized sterile water. Add 20 µl of this solution in 30 ml deionized sterile water to obtain a solution ready for use.

Alternatively, toluidine blue powder (Sigmal Aldrich) 10 mg is dissolved in 10 ml MQ water (mother solution). Dilute 20 µl in 30 ml MQ water.

EXAMPLE 2

Analysis of Body Fluid
Sample: Lumbar puncture and 1 ml cerebrospinal fluid. Centrifuged 3000 g for 5 minutes.
    Gel: The gel according to Recipe 1
    Add 100 µl CSF to the tube
    Wait for 2 minutes
    Remove excess fluid, e.g. by sterile cotton tip applicator
    Add 200 µl Toluidine blue
    Observe the colour change by eye or read by a table spectrophotometer.
    A red colour indicates a negative result and a blue colour indicates a positive result.

Optionally, one or more reference solutions of known HGF content is used to evaluate the result. A negative reference may be e.g. water or PBS. A positive reference may be a body fluid sample or a commercial HGF containing product, with known HGF content.

EXAMPLE 3

Analysis of Commercial Product
Sample: Antithrombin III UF2 (Octapharma, Sweden)
Gel: The gel according to recipe 3
50 µl sample was added to the wells.
100 µl Toluidine blue indicator solution was added.

TABLE 1

| Dilution UF2 | Colour | Result | Spectrophotometer (filter 620) |
|---|---|---|---|
| 1:1 | Blue | Pos++ | 0.110 |
| 1:2 | Blue | Pos++ | 0.107 |
| 1:4 | Blue | Pos++ | 0.093 |
| 1:8 | Light blue | Pos+ | 0.085 |
| 1:16 | Red | neg | 0.080 |
| 1:32 | Red | neg | 0.080 |
| MQ | Red | neg | 0.079 |

Addition of HSPG or fragmin prior to addition of indicator solution gave negative results.

TABLE 2

| | Colour | Result |
|---|---|---|
| Dilution UF2 + 2 µl HSPG | | |
| 1:1 | red | neg |
| 1:2 | red | neg |
| 1:4 | red | neg |
| 1:8 | red | neg |
| 1:16 | red | neg |
| 1:32 | red | neg |
| Dilution UF2 + 2 µl low molecular heparin 5000 E/ml | | |
| 1:1 | red | neg |
| 1:2 | red | neg |
| 1:4 | red | neg |
| 1:8 | red | neg |

TABLE 2-continued

| | Colour | Result |
|---|---|---|
| 1:16 | red | neg |
| 1:32 | red | neg |

EXAMPLE 4

Analysis of a Number of Commercial Products

An analysis of a number of commercially available HGF containing products were made. The binding of HGF to a monoclonal anti-HGF antibody and to HSPG were analysed by SPR in a Biacore® instrument (GE Healthcare, Sweden). Two runs per product were made. The products were also analysed with the method according to the invention (Dexakt) and in the cell based CCL-53.1 assay. The results are summarised in Table 3.

TABLE 3

AT III products controlled for presence of biologically active HGF by Biacore ® and Dexakt. Products with high affinity to monoclonal anti-HGF antibody and decreased affinity to HSPG in Biacore ® system and negative DEXAKT test had no biological activity on CCL-53.1 in-vitro test.

| | Monoklonal anti HGF | HSPG | Moklonal anti HGF | HSPG | DEXAKT | CCL-53.1 cells |
|---|---|---|---|---|---|---|
| Atenativ Pharmacia 50 E/ml 1:1 PBS | 1762 | 53 | 1759 | 49 | negative | negative |
| Kybernin HS (2004) 50 E/ml 1:1 PBS | 238 | 8 | 270 | 6 | negative | negative |
| Kybernin H (2009) 50 E/ml 1:1 PBS | 731 | 2 | 804 | 2 | negative | negative |
| Grifolds 50 E/ml 1:1 PBS | 821 | 14 | 901 | 13 | negative | negative |
| Immuno 50 E/ml 1:1 PBS | 3055 | 2386 | 3145 | 2259 | positive | Motogen effect + |
| UF1 C924A201 1:1 PBS | 1503 | 378 | 1655 | 381 | positive | Motogen effect ++ |
| UF2 C223A203 1:1 PBS | 1141 | 88 | 1253 | 104 | positive | Motogen effect + |

EXAMPLE 5

Analysis of Urine Samples

Growth of bacteria in urine culture is an indication for diagnosis UTI and antibiotic treatment. In some cases the infectious focus is not easy to determine because the patient might have distal UTI but still the real infectious focus is somewhere else. In such cases positive Dexakt test verifies urine as an infectious focus. The therapy might be modified as well by repeating tests. We have controlled rapid test in urine of patients with positive and negative cultures and controlled the results with deep stick test and SPR (Table 4-5). As shown Dexakt might distinguish an organ injury caused by infection in the kidneys (urinary tract infection=UTI) from other causes of disease. The cases in which urine was tested by Dexakt, dip stick as well as by SPR are presented below in Tables 4-5 and case report 1.

TABLE 4

Negative control urine.

| Age/Sex | Dexakt | Mono | HSPG | Blood stick | Protein stick | WBC stick | Final Dignosis |
|---|---|---|---|---|---|---|---|
| 24/male | neg | −93.4 | −5.9 | neg | neg | neg | Blood donor |
| 65/female | neg | −58.3 | −11.2 | neg | neg | neg | Blood donor |
| 64/female | neg | −12 | −1.5 | neg | neg | neg | Blood donor |
| 42/male | neg | −16.3 | −1.4 | neg | pos | neg | Blood donor |
| 23/male | neg | −15.9 | −1.6 | neg | neg | neg | Blood donor |
| 22/female | neg | −29.6 | −4.6 | neg | neg | neg | Blood donor |
| 39/male | neg | −15 | −4.9 | neg | neg | neg | Blood donor |
| 39/female | neg | −16 | −7 | pos | neg | neg | Blood donor |
| 60/female | neg | −16 | −4.6 | neg | neg | neg | Blood donor |
| 53/female | neg | −24.8 | −1.4 | neg | neg | neg | Blood donor |
| 61/male | neg | −21.6 | 1.1 | neg | pos | neg | Blood donor |
| 60/female | neg | −17.9 | 5.4 | pos | neg | neg | Blood donor |
| 56/male | neg | −58 | 0.2 | neg | neg | neg | Blood donor |
| 44/female | neg | −11 | −2.9 | pos | neg | neg | Blood donor |
| 55/female | neg | −18 | −3 | neg | neg | neg | Blood donor |
| 34/female | neg | −9 | −5 | neg | neg | neg | Blood donor |
| 22/female | neg | −2 | −1 | neg | neg | neg | Blood donor |
| 34/male | neg | −8.9 | −0.8 | neg | neg | neg | Blood donor |

Neg = negative.
Pos = positive

TABLE 5

Cases in which urine was tested by Dexakt. As seen UTI = urinary tract infection

| Age/Sex | Dexakt | Mono | HSPG | Blood stick | Protein stick | WBC stick | Final Dignosis |
|---|---|---|---|---|---|---|---|
| 21/female | pos | 100.9 | 4.2 | pos | pos | pos | UTI |
| 42/female | pos | 159 | 22.8 | pos | pos | pos | UTI |
| 11/male | pos | −28.2 | 0.3 | neg | pos | neg | Fever of unknown origin |
| 27/female | pos | 28.3 | 6.2 | pos | neg | pos | Asymptomatisc leukocyturia |
| 52/female | pos | 172 | −0.8 | pos | pos | pos | Asymptomatisc leukocyturia |
| 76/male | pos | 78 | 4.6 | pos | pos | pos | UTI |
| 59/female | pos | 218 | 8.5 | Pos | Pos | pos | UTI |
| 29/female | neg | 14.8 | −4.2 | pos | pos | pos | Distal UTI |
| 31/male | neg | −24.1 | −6.7 | neg | neg | neg | Anal fistel |
| 50/female | neg | −34.6 | −8.1 | pos | neg | neg | Control after UTI |
| 11/male | neg | −19.3 | −45.8 | neg | pos | neg | Fever of unknown origin |
| 44/male | neg | −16 | −7 | neg | pos | neg | Hepatitis C |
| 28/male | neg | −6 | −1.6 | neg | neg | neg | Allergy |
| 6/male | neg | −99.8 | −2.3 | neg | neg | neg | Dysuria |
| 2/male | neg | −32 | −3.9 | neg | neg | neg | Fever of unknown origin |
| 35/male | neg | −10.3 | −1.8 | neg | neg | neg | Stomach pain |
| 30/female | pos | 48 | 2.6 | Pos | Pos | pos | UTI |

Case Report 1:

77 years old man admitted to the Department of Infectious Diseases. Pain in stomach and fever and Diarrhea. Growth of Clostridie deficile in faeces culture. Received antibiotics but continued fever, intensive pain in stomach and diarrhea. Urine test positive stick for leukocytes and blood. Culture positive Klebsiella pneumonic. Dexakt neg urine. received antibiotics orally. CRP unchanged and increasing afterwards. Several surgeon consultation. Computer tomography with contrast reveals retroperitoneal abscess. Treated by drainage. Conclusion: In spite of positive urine culture Dexact could predict that urinary tract system was not the focus of infection.

EXAMPLE 6

Test of Rapid Test in Patients with Meningitis

It is of highest importance to begin treatment with antibiotics as soon as possible when bacterial meningitis is suspected, since the mortality is increased by 18-30% for every one hour the treatment is postponed. Analyses of cerebrospinal fluid (CSF) is the routine acute method to evaluate the meningitis, counting the white blood cells and lactate in CSF. When suspected, the empirical antibiotic treatment is initiated waiting for culture results. In complicated cases such as patients with brain haemorrhage or after brain surgery it is not possible to rely on cell counts, lactate or even on culture results. Therefore the diagnosis of meningitis is very difficult and nearly all patients receive wide antibiotic treatment to avoid brain injuries caused by infection. A method that can distinguish injuries caused by bacterial infection as complementary test might be of high value in such cases.

To evaluate the test we have used cerebrospinal fluid from patients with meningitis (positive control) compared to patients that have undergone lumbar puncture for other reasons (negative control). Patients with acute bacterial meningitis, had high CRP (>150), CSF polyneuclear pleocytosis and elevated CSF protein. The cultures were positive in CSF and a clinical course as a septic meningitis was seen. Negative control comprised patients who were admitted for other reasons; such as confusion, fatigue, fever and even pneumonia, where meningitis was ruled out by normal CSF. The results from SPR (Biacore) highly correlated to our rapid test. The sensitivity and specificity of tests for acute inflammation in CSF was >95% (Table 6-7, FIG. 1).

TABLE 6

Biacore ® and Dexakt test of CSF in negative controls (normal CSF)

| | C-met | HSPG | mono | D19 | Dexakt |
|---|---|---|---|---|---|
| 1 | 60 | 7 | −1 | 29 | neg |
| 2 | 23 | −1 | −9 | 47 | neg |
| 3 | 1 | −0.1 | −7 | 17 | neg |
| 4 | 19 | 1 | −3 | 26 | neg |
| 5 | 6 | 1 | −5 | 9 | neg |
| 6 | −8 | −5 | −20 | 16 | neg |
| 7 | 44 | 0.3 | −5 | 18 | neg |
| 8 | 4 | 1 | −7 | 11 | neg |
| 9 | −4 | −1 | −14 | 6 | neg |
| 10 | −15 | −3 | −16 | 1 | neg |
| 11 | 14 | −0.3 | −6.2 | 17 | neg |
| 12 | −1 | −2 | −10 | 7 | neg |
| 13 | 1 | −0.4 | 8 | 18 | neg |
| 14 | −5 | −1 | −10 | 20 | neg |
| 15 | 3 | −0.3 | −9 | 18 | neg |
| 16 | −6 | −1 | −11 | 14 | neg |
| 17 | 0 | −1 | −10 | 24 | neg |
| 18 | −9 | −2 | −13 | 2 | neg |
| 19 | −8 | −2 | −11 | 23 | neg |
| 20 | −15 | −2 | −13 | 8 | neg |
| 21 | −15 | −6 | −7 | −16 | neg |
| 22 | −10 | −6 | −50 | −1 | neg |
| 23 | −9 | −0.3 | −44 | 5 | neg |
| 24 | −6 | −4 | −3 | −0.6 | neg |
| 25 | −7 | −4 | −3 | −8 | neg |
| 26 | −57 | −4 | −30 | −0.8 | neg |
| 27 | −4 | −2 | −26 | 14 | neg |
| 28 | −6 | −5 | −3 | −9 | neg |
| 29 | −5 | −4 | −2 | −6 | neg |
| 30 | −4 | −3 | −28 | 8 | neg |
| 31 | −6 | −6 | −3 | −6 | neg |
| 32 | 33 | −1 | −20 | 18 | neg |
| 33 | −3 | −2 | −19 | 3 | neg |
| 34 | 10 | −1 | −16 | 28 | neg |
| 35 | 50 | 2 | −4 | 40 | neg |
| 36 | −18 | −2 | −22 | −4 | neg |
| 37 | −24 | −4 | −3 | −6 | neg |
| 38 | −0.7 | −1 | −22 | 9 | neg |
| 39 | −16 | −2 | −26 | −2 | neg |
| 40 | −7 | −1 | −2 | −1 | neg |
| 41 | −10 | −1 | −2 | 0.4 | neg |
| 42 | −9 | −2 | −2 | 1.6 | neg |
| 43 | −15 | −3 | −25 | 3 | neg |
| 44 | −11 | −3 | −22 | 10 | neg |

TABLE 7

Biacore ® and Dexakt control of CSF in positive controls (meningitis).

| C-met | HSPG | mono | D19 | DEXAKT | 620 nm | Culture | CSF LPK | CSF lactate |
|---|---|---|---|---|---|---|---|---|
| 151 | 23 | 47 | 60 | pos | 0.134 | group A Strep | 1400 | 11.3 |
| 5 | −5 | −7 | −0.7 | neg | 0.075 | *Candida tropicalis* | 10 | 2.5 |
| 272 | 12 | 64 | 98 | pos | 0.082 | pnc | 2162 | nd |
| 164 | 18 | 11 | 54 | pos | 0.081 | *staf aureus* | 618 | nd |
| 73 | 16 | 23 | 66 | pos | 0.08 | CNS | 760 | nd |
| 1972 | 14 | 930 | 257 | pos | 0.133 | enterococcus | 6350 | 4.2 |
| 353 | 20 | 226 | 222 | pos | 0.93 | pnc | | 10.5 |
| 316 | 19 | 161 | 185 | pos | 0.128 | *Strep mitis* | nd | nd |
| 104 | 56 | 73 | nd | pos | nd | CNS | 560 | 16.9 |
| 215 | 81 | 142 | nd | pos | nd | *Strep intermedius* | 128 | 8.6 |
| 201 | 89 | 124 | nd | pos | nd | neg | 412 | |
| 88 | 63 | 56 | nd | pos | nd | grupp A *Strep* | 1210 | 10.3 |
| 37 | 29 | 43 | nd | pos | nd | HI | 802 | 4.5 |
| 105 | 89 | 81 | nd | pos | nd | *E fecalis* | 1560 | |
| 300 | 119 | 202 | nd | pos | nd | CNS | 2880 | 8.2 |
| 32 | 56 | 30 | nd | pos | nd | CNS | 280 | |
| 3 | 10 | 29 | nd | pos | | propionbak | 290 | 3.2 |

C-Met = binding to channel immobilised by recombinant c-met chimera på Biacore,
HSPG = binding affinity to channel immobilised by heparan sulphate proteoglycan in Biacore,
Mono = binding to the channel immobilised by monoclonal anti-HGF antibody in Biacore,
D19: binding to the channel immobilised by antibody against beta chain of HGF in Biacore.
nd = non-defined

EXAMPLE 7

Test of the Dexakt Test in Feces

Patients who are admitted to the hospital because of an acute episode of diarrhea are isolated until they are recovered or until it is clear that they do not suffer from a transmittable gastroenteritis. It has happened that in some cases needing acute surgical intervention, the diagnosis and treatment has been postponed because the patients were admitted with atypical symptoms such as diarrhea. Levels of HGF in faeces increase during acute infectious gastroenteritis but the HGF levels are low in unspecific diarrhea (PCT application Ser. No.p16114PC-00). We believe that the quality or form of HGF in the faeces is another marker that contributes to diagnosis of the nature of bowel diseases. Thus, determination of HGF in faeces was presented as a diagnostic marker in bowel diseases (Patent WO 2005/031365 A2).

During 2009, 3600 patients were admitted at the University Hospital in Linköping for diarrhea. Nine hundred eighty five patients were isolated at the Department of Infectious diseases but only 66 patients had verified transmittable diarrhea. Regarding to high costs of isolation (3500 SEK/day) it is easy to calculate advantages in a reliable test that can distinguish transmittable diarrhea before culture results are available in at least three days.

Figure 2:
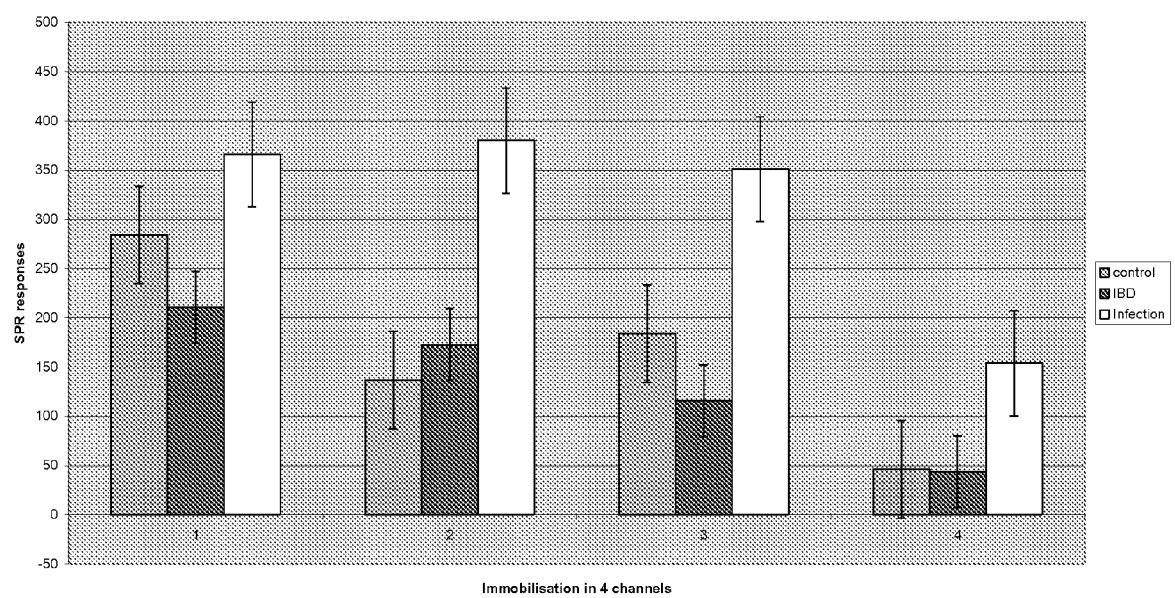
FIG. 2: Binding affinity to channels in SPR chip immobilized by c-met receptor chimera (1), anti-HGF monoclonal antibody (2), anti TGF beta monoclonal antibody (3) and HSPG (4) is compared in three groups with clostridium deficile positive diarrhea (n=20), Inflammatory bowel disease (n=33) and healthy controls (n=7).

Test of Dexakt was performed on stool for evaluation in 11 cases and the results were verified by Biacore® test of faeces. Dexakt might predict transmittable diarrhea with high specificity and sensitivity. The results correlated well with Biacore® tests (not shown). The table presenting results from patients and Case report 2 and FIG. 2 is presented.

TABLE 8

Test of faeces in cases and the diagnosis after the culture results were available

| Age/sex | Dexakt | WBC | Faeces culture | Final Diagnosis |
|---|---|---|---|---|
| 23/female | pos++ | 7.3 | negative | Transmittable diarrhoea |
| 59/female | pos++ | 7.2 | negative | Transmittable diarrehea |
| 51/male | neg | | negative | Inflammation bowel |
| 80/male | Pos+ | 20 | negative | Suspect virual diarrhea |
| 59/male | negative | 10.4 | *campylobacter* | Susp Crohn disease |
| 38/female | Pos++ | 12.2 | *campylobacter* | Transmittable diarrhea |
| 23/female | Pos++ | 12.3 | negative | Transmittable diarrhea |
| 56/female | Pos++ | Non-defined | *Clostridium deficile* | *Clostridium deficile* |
| 38/male | negative | 4.5 | negative | Inflammatory bowel diseases |
| 57/female | Pos+ | 16.4 | negative | Calici virus |
| 59/female | Pos+ | 1.6 | negative | Calici virus |

Case Report 2

Otherwise healthy 59 years old man. Admitted to the Department of Infectious Diseases because of constant diarrhea and fever. August 2009. Dexakt test faeces negative but it grows *Campylobacter* in the faeces cultures. Treated as infectious diarrhea with intravenous antibiotics. The clinical status not changed. The computer tomography bowel shows terminal ileitis. Suspect Crohn disease. Planned Coloscopy. Denied by the physician. Patient dismissed. Fever, joint infusion. Admitted again. No diarrhea. High sedimentation rate. Diagnosed as reactive arthritis. Continued feber after dismissed. Several antibiotic periods. Prednisolon. Heart infarction in October, PCI. No real recovery. Prostatitiis. Treated with oral antibiotics several times. Anemia, rectal bleeding. Colocsopy planned now.

Conclusion: Dexakt test could predict a chronic inflammatory process in spite of positive culture.

The invention claimed is:

1. A method for determining the presence, absence or amount of biologically active or inactive HGF in a sample, comprising the steps:
   a) bringing the sample in contact with a gel comprising a Hepatocyte Growth Factor (HGF) binding component of the extracellular matrix or cell membrane that can bind toluidine blue;
   b) adding toluidine blue to the gel wherein the toluidine blue changes color when bound to said HGF binding component of the extracellular matrix or cell membrane; and
   c) determining and correlating the colour of the toluidine blue in the gel and/or a liquid in contact with the gel with the presence, absence or amount of biologically active HGF in the sample.

2. A method according to claim 1, wherein the HGF binding component is a proteoaminoglycan or glucosaminoglycan.

3. A method according to claim 1, wherein the HGF binding component is heparan sulphate proteoglycan or dextran sulphate.

4. A method according to claim 1, wherein the gel further comprises chitosan.

5. A method according to claim 1, further comprising a step of washing the gel before addition of toluidine blue.

6. A method according to claim 1, wherein said sample is a tissue, body fluid or excrement sample from a patient.

7. A method according to claim 1, wherein said sample is from a pharmaceutical product.

* * * * *